United States Patent [19]

Willey et al.

[11] Patent Number: 5,510,477

[45] Date of Patent: Apr. 23, 1996

[54] PROCESS FOR THE ACYLATION OF LACTAMS

[75] Inventors: Alan D. Willey; Larry E. Miller, both of Cincinnati, Ohio

[73] Assignee: The Procter & Gamble Company, Cincinnati, Ohio

[21] Appl. No.: 204,113

[22] Filed: Mar. 1, 1994

[51] Int. Cl.$^6$ .......... C07B 43/06; C07D 223/10; C07D 207/12

[52] U.S. Cl. .......... 540/529; 540/451; 540/200; 546/245; 548/245; 548/540

[58] Field of Search .................. 540/451, 529; 546/245; 548/540

[56] References Cited

U.S. PATENT DOCUMENTS

| | | | |
|---|---|---|---|
| 3,865,814 | 2/1975 | Lussi et al. | 260/239.3 |
| 3,988,318 | 10/1976 | Copes et al. | 260/239.3 |
| 4,113,735 | 9/1978 | Kurkov | 548/540 |
| 4,221,789 | 9/1980 | Rodriguez et al. | 424/244 |
| 4,608,201 | 8/1986 | McCollum | 540/529 |

FOREIGN PATENT DOCUMENTS 1102521  12/1963  United Kingdom.

OTHER PUBLICATIONS

Ser. No. 08/064,562 filed on May 20, 1993 to Willey et al.
Ser. No. 08/064,623 filed on May 20, 1993 to Willey et al.
Ser. No. 08/064,624 filed on May 20, 1993 on Willey et al.
Ser. No. 08/082,270 filed on Jun. 24, 1993 to Willey et al.
Ser. No. 08/151,085 filed on Nov. 12, 1993 to Burns et al.
Ser. No. 08/196,322 filed on Feb. 15, 1994 to Burns et al.

*Primary Examiner*—Mark L. Berch
*Attorney, Agent, or Firm*—M. D. Jones; J. J. Yetter; K. W. Zerby

[57] ABSTRACT

High quality acyl lactam imides are prepared by reacting an acyl lactam of the formula

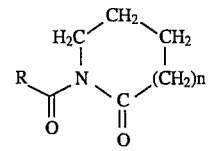

where 5 carbon atoms and an acylating acid of the formula $R'CO_2H$ or by reacting a lactam, an anhydride of the formula $(RCO)_2O$ where R is 1 to 5 carbon atoms and an acylating acid, preferably in the presence of a base catalyst. The process affords acyl lactam imides in high yield and at lower reaction temperatures by providing for the removal of volatile carboxylic acid by-products under vacuum or by the use of a stripping gas. The acyl lactam imides are particularly suited for use as bleach activators in detergent compositions.

1 Claim, No Drawings

PROCESS FOR THE ACYLATION OF LACTAMS

TECHNICAL FIELD

The present invention relates to a method for the preparation of lactam imides which are useful as bleach activators in detergent compositions.

BACKGROUND OF THE INVENTION

The production of acyl lactams can be difficult because it, many times, involves the formation of the anhydride or acid chloride of the acylating acid prior to the acylating reaction. Further, when the acyl lactam is to be used in industrial applications, such as for use as bleach activators in detergent compositions, the reaction by-products, i.e., HCl, and NaCl, must be removed from the acyl lactam product. Consequently, such typical reactions can be costly and unacceptable for industrial applications. Furthermore, the reaction by-products can be difficult to dispose of and can contribute to environmental concerns. A need, therefore, exists for a process that can be conducted using relatively simple chemistry and which avoids costly by-product removal.

Moreover, to avoid long reaction times, acid chloride, acid anhydride, and transacylation chemistry frequently must be conducted a relatively high temperatures which leads to low yields, to polymerization by-products and to coloration problems in the product. To avoid the need for a costly purification step, the process should provide products in high yield and which are substantially pure and with good color. The present invention solves problems associated with known high temperature reactions.

BACKGROUND ART

U.S. Pat. No. 4,608,201, issued Aug. 26, 1986, discloses a process for preparing lactam imides that involves, for example, reacting a lactam, a non-volatile carboxyl group-containing material, and an anhydride of a volatile carboxylic acid. The present invention provides a substantial improvement over the art-disclosed process, especially with regard to the purity and yield of the product.

U.K. 1,192,521, published Feb. 7, 1968, discloses a process which comprises reacting a carboxylic acid with lactam reactants to form acyl lactams.

SUMMARY OF THE INVENTION

The present invention relates to a process for making lactam imides, preferably with the aid of a catalyst. The resulting lactam imides are particularly suited for use as bleach activators. The process comprises the steps of:

a) heating an acyl lactam of a volatile acid and an acylating acid to form the acyl lactam imide and a volatile acid at a temperature of about 130° to about 170° C. preferably from about 140° to about 165° C., most preferably from about 150° to about 165° C.;

b) removing the volatile acid formed during the reaction of step (a) such that less than about 5, preferably less than about 3, more preferably less than about 1, mole percent of the volatile acid is present in the reaction mixture; and c) recovering the acyl lactam imide product.

The preferred process is represented by the following reaction:

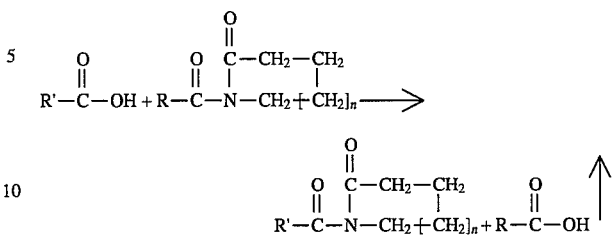

wherein R' is from about 6 to about 19 carbon atoms, R is from about 1 to about 5 carbon atoms, and n is 0 to about 8.

Alternatively, the acyl lactam may be formed in situ by reacting an anhydride with a lactam and the acylating acid. This process comprises the steps of:

a) heating an anhydride of a volatile acid, an acylating acid, and a lactam at a temperature of about 130° to about 170° C., preferably from about 140° to about 165° C., most preferably from about 150° to about 165° C. to form the acyl lactam imide and a volatile acid of the anhydride;

b) removing the volatile acid formed during the reaction of step (a) such that less than about 5, preferably less than about 3, more preferably less than about 1, mole percent of the volatile acid is present in the reaction mixture; and c) recovering the acyl lactam imide product.

The process is preferably represented by the reaction:

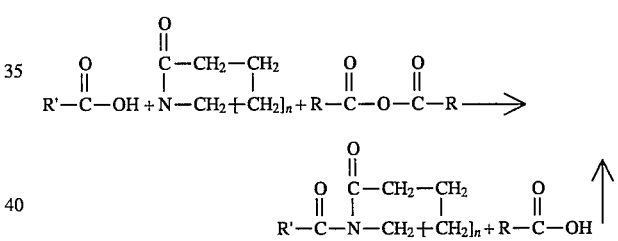

wherein R', R and n are as defined above.

Contrary to the teachings of U.S. Pat. No. 4,608,201, a minimum of volatile carboxylic acid formed in step (a) should be present in the reaction mixture. Less than about 5 mole percent, more preferably no more than about 1 mole percent of volatile acid should be present during the reaction of the acyl lactam and acylating acid. It has been found that the presence of volatile acid during the reaction process leads to reduced yields and undesirable polymerization.

To ensure the rapid and substantial removal of the volatile carboxylic acid, it is preferred that the distillation step (b) be conducted under a vacuum at a pressure below about 50 mm Hg, preferably below about 30 mm Hg. Alternatively, step (b) may be conducted with the use of a stripping gas, e.g., an inert gas such as nitrogen, (preferably with a flow of about 0.005 to about 0.05 l/hr/m$^3$, more preferably from about 0.015 to about 0.03 l/hr/m$^3$). The use of an azeotropic distillation system may be used but is not recommended. To be commercially acceptable, the azeotropic agent must be recycled which requires an expensive process to separate the agent from the volatile acid.

The acylating acids are selected from the group consisting of benzoic acid, substituted benzoic acids, C7–C20 linear or branched saturated or unsaturated fatty acids, and mixtures thereof. The most preferred acylating acids are selected from the group consisting of benzoic, substituted benzoic, and C7–C12 fatty acids.

Preferred lactam reactants are selected from the group consisting of caprolactams, valerolactams, 2-azacyclooctanone, 2-azacyclotridecanone, pyrolidone, and their acetyl derivations. Particularly preferred lactams are selected from the group consisting of caprolactams, valerolactams, and their acetyl derivations.

Preferably, the anhydride of a volatile acid has from about 1 to about 6 carbon atoms. Particularly preferred anhydrides are carboxylic acid anhydrides, especially acetic anhydride.

Preferably the above processes can further comprise the aid of a catalyst. The preferred catalysts are basic, such as titanates, alkali, alkaline earth salts, zinc, iron, aluminum and nickel salts, and oxides, including titanium tetrapropoxide, magnesium oxide, and zinc oxide. Especially preferred are alkali or alkaline earth salts and zinc salts of the volatile carboxylic acid and/or acylating acid. Most preferred catalysts are selected from the group consisting of sodium acetate, magnesium acetate, aluminum acetate, and zinc acetate. The catalyst is present at a level comprising from about 0.01 to about 5 mole percent, preferably from about 0.1 to about 2.5 mole percent, most preferably from about 0.5 to about 1.5 mole percent of the reacting acid.

All percentages, ratios, and proportions herein are by weight, unless otherwise specified. All references disclosed are hereby incorporated by reference.

DETAILED DESCRIPTION OF THE INVENTION

The process of this invention employs reactants and catalysts which are well known in the art. However, use of these materials in the manner disclosed herein provides benefits such as superior yield, faster reaction times, and/or minimum polymerization. The following is intended to assist the manufacturer in the practice of the invention.

In one preferred embodiment of the process, the reactants comprise benzoic acid and an acyl valerolactam, preferably acetyl valerolactam:

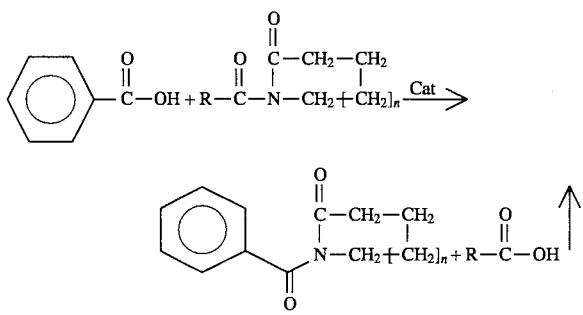

wherein n=1, and R is a C1–C5 alkyl group.

In a another preferred process, the reactants comprise acetic anhydride, benzoic acid, and caprolactam:

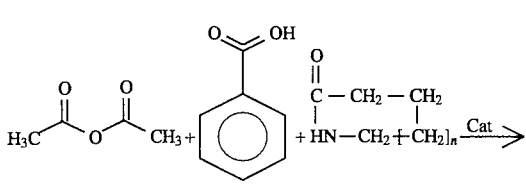

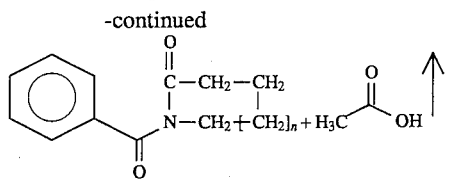

wherein n=2.

The above process may be conducted with or without the aid of a base catalyst. The use of an acid catalyst in the present process has been found to lead to side reactions, lower yields, and poor color. A distillation column may be used to enable removal of the volatile acid while maintaining the level of reactants.

EXAMPLE I

Synthesis of Benzoyl Caprolactam via Transacylation with Argon Sweep—A 500 ml 3 neck round bottom flask, equipped with a heating mantle, magnetic stirrer, distillation head/reflux condenser and Argon sweep (set at approximately 50 l/hr over the reaction mixture), is charged with 0.375 moles benzoic acid, 1.125 moles acetyl caprolactam and 0.00375 moles sodium acetate. The flask is well insulated with fiber glass wool and foil. The solution is refluxed at 155° C. for 10 hours to yield 180 g of light yellow oil. A sample is analyzed via gas chromatography and is shown to be approximately 32% benzoyl caprolactam, which represents approximately 70% yield.

EXAMPLE II

Synthesis of Benzoyl Caprolactam via Transacylation with Vacuum from Acetic Anhydride and Caprolactam—A 500 ml 3 neck round bottom flask, equipped with heating mantle, magnetic stirrer, 18 stage vacuum jacketed Snyder column (insulated with fiber glass wool), and distillation head/reflux condenser, is charged with 0.55 moles acetic anhydride, 0.50 moles caprolactam, 0.50 moles benzoic acid and 0.0035 moles sodium acetate. The mixture is refluxed at 155–165° C. for 7 hours. During the reaction, the system is placed under a vacuum of approximately 25 mm Hg. Gas chromatography analysis shows that the resulting light yellow oil is approximately 70% benzoyl caprolactam.

EXAMPLE III

Synthesis of Benzoyl Caprolactam via Transacylation with Vacuum from Acetyl Caprolactam—A 250 ml 3 neck round bottom flask, equipped with heating mantle, magnetic stirrer, 18 stage vacuum jacketed Snyder column (insulated with fiber glass wool), and distillation head/reflux condenser, is charged with 0.2 moles acetyl caprolactam, 0.20 moles benzoic acid, and 0.002 moles zinc acetate. The mixture is refluxed at 155–165° C. for 7 hours. During the reaction, the system is placed under a vacuum of approximately 25 mm Hg. Gas chromatography analysis shows that the resulting oil is approximately 60% benzoyl caprolactam.

EXAMPLE IV

Example I is repeated without the use of a catalyst, and the reactants are refluxed for approximately 7 hours at a temperature of about 200° C. The resulting product comprises about 20%–40% polymer by-product and only about 24% benzoyl caprolactam.

EXAMPLE V

Example II is repeated with a vacuum of 100 mmHg. A yield of about 30% benzoyl caprolactam is observed.

EXAMPLE VI

Example III is repeated with a vacuum of 100 mmHg. A yield of about 30% product is observed.

EXAMPLE VII

An acid catalyst, about 1 mole percent p-toluene sulfonic acid, is substituted for the sodium acetate in Example I. A yield of about 20% benzoyl caprolactam and at least about 40% undesirable polymers is observed. The benzoyl caprolactam is black in color.

EXAMPLE VIII

An acid catalyst, about 1 mole percent sulfuric acid, is substituted for the sodium acetate in Example I. A yield of about 15% benzoyl caprolactam and at least about 40% undesirable polymers is observed. The benzoyl caprolactam is black in color.

EXAMPLE IX

A granular detergent composition is prepared comprising the following ingredients.

| Component | Weight % |
| --- | --- |
| $C_{12}$ linear alkyl benzene sulfonate | 22 |
| Phosphate (as sodium tripolyphosphate) | 30 |
| Sodium carbonate | 14 |
| Sodium silicate | 3 |
| Benzoyl Caprolactam | 5 |
| Sodium percarbonate | 10 |
| Ethylenediamine disuccinate chelant (EDDS) | 0.4 |
| Sodium sulfate | 5.5 |
| Minors, filler* and water | Balance to 100% |

*Can be selected from convenient materials such as $CaCO_3$, talc, clay, silicates, and the like.

Aqueous crutcher mixes of heat and alkali stable components of the detergent composition are prepared and spray-dried, and the other ingredients are admixed so that they contain the ingredients tabulated at the levels shown.

The detergent granules with bleach activator are added together with 5 lb. (2.3 kg) of previously laundered fabrics to an automatic washing machine. Actual weights of detergent and bleach activator are taken to provide a 950 ppm concentration of the former and 50 ppm concentration of the latter in the 17 gallon (65 l) water-fill machine. The water used has 7 grains/gallon hardness and a pH of 7 to 7.5 prior to (about 9 to about 10.5 after) addition of the detergent and bleaching system. The fabrics are laundered at 35° C. (95° F.) for a full cycle (12 min.) and rinsed at 21° C. (70° F.).

What is claimed is:

1. A process comprising the steps of:
   a) heating acetic anhydride, benzoic acid, and caprolactam at a temperature of about 130° to about 170° C. to form volatile acetic acid and benzoyl caprolactam;
   b) removing the acetic acid formed during step (a) such that less than about 5 mole percent of acetic acid is present in the reaction mixture; and
   c) recovering the benzoyl caprolactam product.

* * * * *